United States Patent [19]

Johnson, IV et al.

[11] Patent Number: 5,133,343

[45] Date of Patent: * Jul. 28, 1992

[54] APPARATUS FOR SUPPORTING AN INHALER

[76] Inventors: John J. Johnson, IV, 505 San Mateo, N.E., Albuquerque, N. Mex. 87108; John J. Johnson, Jr., 720 University Ave., Las Vegas, N. Mex. 87701

[*] Notice: The portion of the term of this patent subsequent to Feb. 14, 2006 has been disclaimed.

[21] Appl. No.: 230,694

[22] Filed: Aug. 5, 1988

Related U.S. Application Data

[63] Continuation of Ser. No. 45,423, May 4, 1987, abandoned, which is a continuation-in-part of Ser. No. 764,189, Aug. 9, 1985, abandoned.

[51] Int. Cl.$^5$ .................................... A61M 15/00
[52] U.S. Cl. ...................... 128/200.23; 128/203.15; 128/204.26
[58] Field of Search ............... 128/200.23, 203.15, 128/200.14, 204.21, 204.23, 204.26

[56] References Cited

U.S. PATENT DOCUMENTS

| | | | |
|---|---|---|---|
| 3,456,644 | 7/1969 | Thiel | 128/200.23 |
| 3,456,645 | 7/1969 | Brock | 128/200.23 |
| 3,565,070 | 2/1971 | Hanson et al. | 128/200.23 |
| 3,636,949 | 1/1972 | Kropp | 128/200.23 |
| 3,789,843 | 2/1974 | Armstrong et al. | 128/200.23 |
| 3,826,413 | 7/1974 | Warren | 128/200.23 X |
| 4,414,972 | 11/1983 | Young et al. | 128/200.23 |
| 4,576,157 | 3/1986 | Raghuprasad | 128/200.23 |
| 4,648,393 | 3/1987 | Landis et al. | 128/200.23 |
| 4,803,978 | 2/1989 | Johnson, IV et al. | 128/200.23 |

Primary Examiner—William E. Kamm
Assistant Examiner—J. P. Lacyk
Attorney, Agent, or Firm—Cahill, Sutton & Thomas

[57] ABSTRACT

Apparatus, having an outlet port insertable within a user's mouth, has housed therein an automatically actuated commercially available and replaceable inhaler for discharging a medicated vapor through the outlet port into the user's mouth upon inhalation. The apparatus includes a housing having ribs for slidably supporting the inhaler, which inhaler is a cylindrical aerosol can containing medication under pressure. The housing is detachably attached to the apparatus to permit replacement of the inhaler and for cleaning purposes. A conduit extends from the housing for insertion into a user's mouth. On inhalation by a user, the apparatus will be actuated to slidably reposition the inhaler and effect discharge of a spray of medication through the conduit into the user's oral cavity and lungs.

10 Claims, 1 Drawing Sheet

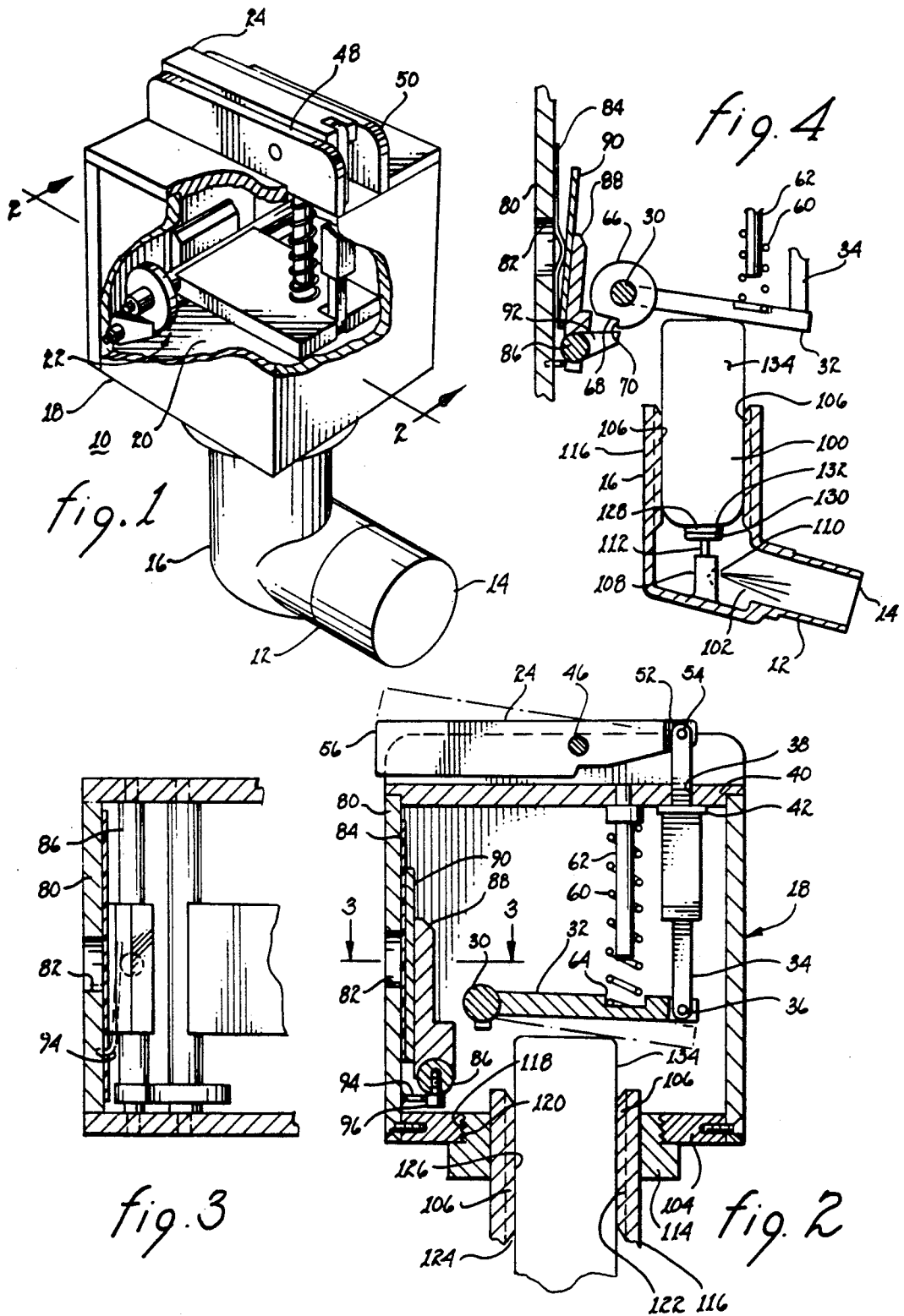

APPARATUS FOR SUPPORTING AN INHALER

CROSS REFERENCE TO RELATED APPLICATIONS

This is a continuation of application Ser. No. 045,423, filed May 4, 1987, now abandoned, which is a continuation in part application of a copending application entitled "APPARATUS FOR ACTUATING AN INHALER", filed Aug. 9, 1985, assigned Ser. No. 764,189 and describing an invention by the present inventor now abandoned; this application is related to U.S. Pat. No. 4,803,978 issued Feb. 14, 1989, filed Aug. 21, 1987 and describing an invention made by the present inventor.

BACKGROUND OF THE INVENTION

1. Field of the Invention

The present invention relates to respiratory devices and, more particularly, to apparatus responsive to inhalation for actuating commercially available inhalers capable of discharging a medicated vapor spray.

2. Description of Related Art

Many persons suffering from emphysema and other respiratory diseases or disabilities have difficulty breathing from time to time, depending upon the activity engaged in, degree of inflammation of respiratory tissues and other stresses. A number of medications are usable to alleviate the debilitating symptoms or to restore normal breathing. Many of these medications are dispensed from aerosol-like dispensers as a vapor to be inhaled directly into the lungs. The dispenser may include an outlet port to be placed in the user's mouth in sealed relationship to ensure passage of the medication down the user's throat and into his lungs. Actuation of these devices generally requires a compressive force to be exerted by a user's hand after the outlet port is placed within the mouth.

For many persons, actuation of the device is of no moment. However, others who have a need for such inhalers may also suffer from the debilitating effects and limitations attendant arthritic hands. Some of these persons no longer have the requisite strength or manual dexterity to compress the inhalers. Yet other persons may become too disoriented or otherwise not be capable of using the inhalers when needed which debility may be caused in part by the difficulty experienced in breathing.

In an effort to overcome the need to compress an inhaler in order to use it, numerous devices have been developed as attachments to such inhalers. Some of these devices require actuation of a mechanical element which directly or indirectly compresses the inhaler to provide discharge of the medicated vapor. Such devices are not readily usable by persons who are not fully dexterous or persons who may become disoriented due to or as a result of breathing difficulties. Yet other devices have a triggering mechanism which is manually actuated. Upon actuation, the medicated vapor is discharged from the inhaler. Again, such devices require a degree of dexterity which may not be available to every actual or potential user due to physical frailty or disorientation.

The following U.S. Pats. Nos. disclose prior art devices of the type described above: 3,157,179, 3,178,748, 3,356,088, 3,456,644, 3,456,646, 3,656,070, 3,636,949, 3,789,843, 3,814,297 and 3,826,413.

SUMMARY OF THE INVENTION

The present invention includes a sealed container having replaceably located therein a commercially available inhaler and an outlet port in fluid communication with the inhaler to discharge automatically a medicated vapor directly into the user's lungs. A valve, responsive to a below atmospheric pressure within the apparatus, releases a plate in a cocked state pending operation of the triggering mechanism initiated by operation of the valve. In operation, a user places the outlet port within his mouth and begins to inhale. The resulting pressure drop within the apparatus actuates the valve of the trigger mechanism detachably attached along a housing to release and unlock the spring loaded plate. The plate, in response to the spring, repositions the inhaler to effect discharge of the medicated vapor spray through the outlet port directly into the user's mouth, throat and lungs.

It is therefore a primary object of the present invention to provide a device for actuating an inhaler in response to inhalation by a user.

Another object of the present invention is to provide a device which requires only that the outlet port thereof be placed within the user's mouth to obtain a discharge of medicated vapor upon inhalation.

Yet another object of the present invention is to provide a device for automatically discharging a medicated vapor at the moment of need.

Still another object of the present invention is to provide a method for actuating an inhaler in response to inhalation by a user.

A further object of the present invention is to provide a detachably attached housing for slidably supporting an inhaler.

A still further object of the present invention is to provide a method for actuating an inhaler to discharge medicated vapor into the mouth and lungs of a user.

A yet further object of the present invention is to provide a device capable of receiving and actuating most of the commercially available inhalers.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 is a partially cut away isometric view of the present invention;

FIG. 2 is a cross-sectional view taken along lines 2—2, as shown in FIG. 1;

FIG. 3 is a partial cross-sectional view taken along lines 3—3, as shown in FIG. 2; and FIG. 4 is a cross-sectional view illustrating the operative elements in the uncocked state.

DESCRIPTION OF THE PREFERRED EMBODIMENT

Referring to FIG. 1, there is shown an apparatus 10 having a conduit 12 terminating at an outlet port 14. The conduit and outlet port are sized to permit placement within a user's mouth and without meaningful restriction of a medicated vapor discharged therethrough. A cylindrical housing 16 supports therein an inhaler in fluid communication with outlet port 14. An enclosure 18, supported upon housing 16, defines a chamber 20 within which a triggering mechanism, generally referenced by numeral 22, is housed. A rocker arm 24 is pivotally located upon enclosure 18 for cocking the actuating mechanism attendant the inhaler.

Referring primarily to FIG. 2, details of the actuating and triggering mechanisms will be described. A shaft 30 is pivotally mounted in opposed sides of enclosure 18. Plate 32 is rigidly attached to the shaft and is angularly displaced commensurate with rotation of the shaft. A rod 34 is pivotally attached to the free end of plate 32 through a pivot mechanism 36. The rod extends upwardly into penetrable engagement with an aperture 38 located in top 40 of enclosure 18. An annular flange 42 or the like is disposed upon rod 34 to form a seal about aperture 38 when plate 32 is in the cocked position. Rocker arm 24 is pivotally secured at pivot 46 intermediate protective flanges 48, 50 extending upwardly from top 40. End 52 of the rocker arm is pivotally secured to the upper end of rod 34 through pivot mechanism 54. On inspection, it will be noted that on exerting a downward force upon end 56 of the rocker arm, upward rectilinear translation of rod 34 will occur which in turn will angularly displace upward plate 32 to the cocked position. Preferably, the upper surface of the rocker arm will be essentially coincident with the upper edges of adjacent flanges 48, 50 when plate 32 is in the cocked position.

An ongoing downward force is exerted upon plate 32 by coil spring 60 secured to and extending downwardly from alignment post 62, the latter depending from top 40. A depression 64 is formed in plate 32 to receive and retain the lower end of the coil spring and maintain it in alignment with the post. As depicted in FIGS. 1, 3 and 4, a cam 66 is mounted upon shaft 30. The cam is essentially circular and includes an indentation 68 which indentation incorporates a shoulder 70.

Referring jointly to FIGS. 2, 3 and 4, triggering mechanism 22 will be described in detail. Side wall 80 includes an aperture 82. A flexible membrane 84 is secured adjacent the inner surface of side wall 80 in circumscribing relationship to aperture 82. A shaft 86 is pivotally secured to opposing walls of enclosure 18. An arm 88 is secured to and extends upwardly from shaft 86 for supporting a plate 90. The location and size of plate 90 is selected to overlap the outline of aperture 82 in side wall 80; moreover, in one rotational state of shaft 86, plate 90 is adjacent and parallel to flexible membrane 84.

A sear 92 extends from shaft 86 in general alignment with cam 66 for engaging indentation 68 and bearing against shoulder 70 when plate 32 is in the cocked state. A leaf spring 94 extends from side wall 80 and bears against a bolt 96 or similar protrusion extending downwardly from shaft 86. The force exerted by leaf spring 94 upon shaft 86 will tend to bias plate 90 adjacent membrane 84. As illustrated in FIG. 1, when plate 32 is in the cocked position, shaft 86 is angularly displaced by force of leaf spring 94 to engage sear 92 with indentation 68 in cam 66. The resulting interference between the sear and shoulder 70 will preclude rotation of shaft 30 and commensurate downward angular displacement of plate 32; the plate will be retained in the cocked state by the sear.

Angular rotation of shaft 86 (in the clockwise direction as illustrated in FIG. 4) will withdraw sear 92 from engagement with shoulder 70. Such disengagement will remove the rotational restraint imposed upon plate 32 and the plate will rotate downwardly in response to the force exerted by coil spring 60. Thereafter, sear 92 may rest on the peripheral surface of cam 66. On cocking of plate 32 by exerting a downward force upon rocker arm 24, cam 66 will rotate to permit engagement of the sear with indentation 68. Because of the rotational force exerted by leaf spring 94 upon shaft 86, the sear will be biased counterclockwise into the indentation.

Referring primarily to FIGS. 1, 2 and 4, the mounting of inhaler 100 and the discharge of medicated vapor 102 will be described. Housing 16 is removably attachable to base 104 of enclosure 18 to permit replacement of inhaler 100 within the housing. The attachment may be through a collar 114 circumscribingly attached to vertical portion 116 of housing 16. The collar may be in threaded engagement with base 104 via threads 118, 120, as illustrated. Alternatively, vertical portion 116 may be secured to the base by a friction fit with an appropriately sized aperture in base 104. Other means for detachably attaching the vertical portion of the housing may include a bayonet fitting, a partial turn threaded engagement with or without a detent, etc.

Generally, most commercially available inhalers include a cylindrical canister 134. Such canister is supported by a plurality of ribs 106 in longitudinal alignment with vertical portion 116 and extending radially inwardly from cylindrical surface 122. These ribs are in circumferentially spaced apart relationship to one another. The radial inward extension of radially inward elongated surface 126 of each of the ribs is a function of the diameter of the canister of inhaler 100. The attendant parameters must permit the canister to undergo translational movement within vertical portion 116 in response to repositioning of plate 32 and the force exerted thereby and in response to the bias force associated with a valve 128. Inhaler 100, ribs 106 and interior surface 122 define a plurality of arcuate passageways 124 extending longitudinally within vertical portion 116 of housing 16.

Valve 128 of inhaler 100 is located within neck 130 for releasing flow of medicated vapor from within the inhaler through tube 112 and nozzle 110 in boss 108 in response to relative compressive displacement between the neck and the nozzle. The neck also includes bias means 132 for extending the tube away from the neck on cessation of the compressive force which results in raising of the inhaler relative to boss 108. The boss 108 is formed within conduit 12 to support and bear against tube 112 extending from inhaler 100. The boss includes a passageway for receiving discharge of medicated vapor from tube 112 of the inhaler. It will also be appreciated that inhaler 100 may have a slightly different configuration attendant tube 112 and neck 130 such that nozzle 110 may be incorporated as part of the inhaler. In such event, boss 108 can be a simple pedestal for supporting in fixed relationship the nozzle of the inhaler and to permit the discharge from the nozzle into conduit 12.

To use the device, conduit 12 is placed into the user's mouth and the user begins to inhale. The resulting below atmospheric pressure within conduit 12 is translated through passageways 124 and into chamber 20 of enclosure 18. The resulting difference in pressure between atmospheric pressure and that within chamber 20 will cause flexible membrane 84 in proximity to aperture 82 to flex inwardly. The inward flexure of the membrane, as depicted in FIG. 4, will force plate 90 to rotate clockwise about shaft 86. The resulting commensurate rotation of shaft 86 will disengage sear 92 from indentation 68 in cam 66. Such disengagement permits rotation of the cam and downward angular movement of spring loaded plate 32, which movement will occur in response to the force exerted by coil spring 60. The downward movement of the plate, acting upon canister 134 of inhaler 100, will result in downward movement of the canister with respect to tube 112 positionally maintained by boss 108. The resulting relative displacement between the canister and the tube will open valve 128 located within neck 130 and a measured charge of medicated spray will flow through nozzle 110 of boss 108, into conduit 12 and through outlet port 14.

To reset apparatus 10, end 56 of rocker arm 24 is depressed to a location essentially coincident with that of the upper edges of flanges 48, 50. The resulting release of force upon inhaler 100 will permit canister 134 to rise relative to tube 112 in response to the force of bias means 132 located within neck 130. Additionally, the now existing lack of differential between atmospheric pressure and the pressure within chamber 18 will permit membrane 84 to be essentially planar with side wall 80. In response to the force exerted by leaf spring 94, shaft 86 will rotate counterclockwise to locate plate 90 adjacent membrane 84 and sear 92 into locking engagement with indention 68 of cam 66. The device is now cocked for discharging a further quantity of medicated vapor.

As will become apparent, actuation of apparatus 10 does not require any manual dexterity. Instead, the user need only place conduit 12 within his/her mouth and begin to inhale. This capability is particularly important for those actual and potential users who are physically disabled due to disease or accident and for those who tend to be or may become disoriented at the time medication is needed.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. Apparatus for discharging a charge of medicated vapor from an inhaler directly into the oral cavity and lungs of a user, said apparatus comprising in combination:
   (a) an enclosure;
   (b) an housing in fluid communication with said enclosure and having an outlet port insertable within a user's mouth for channelling the charge of medicated vapor;
   (c) means for detachably attaching said housing with said enclosure for replacing the inhaler;
   (d) support means for supporting the inhaler configured as a cylindrical canister in operative relationship with said enclosure, said support means comprising a plurality of ribs circumferentially disposed about and in longitudinal alignment with the canister for slidably supporting the inhaler;
   (e) an actuating mechanism disposed with said enclosure and responsive to inhalation by a user having said outlet port in the user's mouth upon inhalation, said actuating mechanism including a pivotally mounted member for applying a first force upon the inhaler to urge rectilinear movement of the inhaler in a first direction from a first position to a second position;
   (f) valve means responsive to movement of the inhaler in the first direction for discharging a charge of medicated vapor from the inhaler and through said outlet port;
   (g) nozzle means for directing the charge of vapor through said outlet port;
   (h) means for withdrawing the first force from acting upon the inhaler said withdrawing means including a rod pivotally attached to and extending from said member and a pivotally mounted rocker arm pivotally supporting said rod for drawing said rod in a second direction to disengage said member with the inhaler and for cocking said actuating mechanism; and
   (i) means responsive to withdrawal of the first force for applying a second force upon the inhaler to urge rectilinear movement of the inhaler in the second direction to the first position from the second position.

2. The apparatus as set forth in claim 1 wherein said attaching means comprises engagable threads.

3. The apparatus as set forth in claim 1 wherein the inhaler includes a discharge tube and including a boss located within said housing upstream of said outlet port for supporting the discharge tube and wherein said nozzle means is formed in said boss.

4. The apparatus as set forth in claim 1 wherein said rocker arm is pivotally mounted external to said housing.

5. A method for discharging a charge of medicated vapor from a replaceable inhaler upon inhalation by a user which inhaler includes a canister having a longitudinal axis, said method comprising the steps of:
   (a) locating and slidably retaining the inhaler within a housing having an outlet port;
   (b) placing the outlet port of the housing into the user's mouth;
   (c) creating a below atmospheric pressure within the housing and within an enclosure in fluid communication with the housing by the act of inhaling;
   (d) triggering an actuating mechanism having a pivotally mounted member located within the enclosure in response to the below atmospheric pressure within the enclosure created by inhaling to exert a force upon the inhaler;
   (e) positioning the inhaler located within the housing from a cocked position to a position of use in response to the operation of the pivotally mounted member bearing against and exerting a force upon the inhaler to effect discharge of a charge of medicated vapor from the inhaler, said positioning step including the step of guiding the inhaler within the housing upon a plurality of circumferentially spaced ribs longitudinally aligned with the longitudinal axis of the canister; and
   (f) directing the charge of medicated vapor through the outlet port to the user's mouth; and
   (g) withdrawing the force exerted by the actuating mechanism to permit repositioning of the inhaler from the position of use to the cocked position after discharge of the charge of medication, said step of withdrawing including the steps of pivoting a rocker arm mounted external to the housing, translating a rod in response to pivotal movement of the rocker arm and disengaging the pivotally mounted member from the inhaler in response to translation of the rod.

6. The method as set forth in claim 5 including the step of channelling a flow of air from the enclosure and about the inhaler to the outlet port during inhalation by a user.

7. The method as set forth in claim 5 wherein the housing extends about the inhaler for effecting said step of guiding the inhaler and said step of channelling the flow of air about the inhaler into and out of the enclosure and through the outlet port.

8. The method as set forth in claim 5 wherein said step of detaching and reattaching comprises the step of threadedly disengaging and reengaging the housing with the enclosure.

9. The method as set forth in claim 5 including the steps of detaching and reattaching the housing with the enclosure to replace the inhaler and the steps of slidably removing and replacing the inhaler during exercise of said steps of detaching and reattaching.

10. The method as set forth in claim 5 including the step of exposing a part of the rocker arm upon exercise of said step of triggering.

* * * * *